(12) United States Patent
Okamoto

(10) Patent No.: US 10,863,887 B2
(45) Date of Patent: Dec. 15, 2020

(54) INSERTION DEVICE HAVING UNIVERSAL CORD WITH EXTENDING TRANSMISSION MEMBER

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 396 days.

(21) Appl. No.: 15/959,326

(22) Filed: Apr. 23, 2018

(65) Prior Publication Data

US 2018/0235440 A1 Aug. 23, 2018

Related U.S. Application Data

(63) Continuation of application No. PCT/JP2016/076834, filed on Sep. 12, 2016.

(30) Foreign Application Priority Data

Oct. 28, 2015 (JP) .................................. 2015-212020

(51) Int. Cl.
*A61B 1/00* (2006.01)
*A61B 1/005* (2006.01)

(52) U.S. Cl.
CPC .......... *A61B 1/0016* (2013.01); *A61B 1/0057* (2013.01); *A61B 1/00133* (2013.01);
(Continued)

(58) Field of Classification Search
CPC .............. A61B 1/0016; A61B 1/00156; A61B 1/00133; A61B 1/00154; A61B 1/0057; A61B 1/00078; A61B 1/0055
(Continued)

(56) References Cited

U.S. PATENT DOCUMENTS 5,275,152 A * 1/1994 Krauter ................ A61B 1/0052
138/109
8,801,604 B2 * 8/2014 Hoshino ............ A61B 1/00009
600/132
(Continued)

FOREIGN PATENT DOCUMENTS

EP 3031384 A1 6/2016
EP 3069649 A1 9/2016
(Continued)

OTHER PUBLICATIONS

International Search Report dated Dec. 6, 2016 issued in PCT/JP2016/076834.

*Primary Examiner* — John P Leubecker
(74) *Attorney, Agent, or Firm* — Scully, Scott, Murphy & Presser, P.C.

(57) ABSTRACT

An endoscope includes a flexible tube section including coiled tubes, a motor disposed on a proximal side of the flexible tube section, a driving force transmission unit disposed on a distal side of the flexible tube section, and a drive shaft provided inside the flexible tube section along a long axis, the drive shaft being caused to perform rotation around the long axis by a driving force of the motor and to transmit the rotation of the motor to the driving force transmission unit, where torsional resistance of the flexible tube section around the long axis is set higher than torsional resistance between a relay gear of the motor and a drive gear of the driving force transmission unit through the drive shaft.

8 Claims, 8 Drawing Sheets

(52) U.S. Cl.
CPC ........ *A61B 1/00154* (2013.01); *A61B 1/0052* (2013.01); *A61B 1/0055* (2013.01); *A61B 1/00073* (2013.01); *A61B 1/00078* (2013.01)

(58) Field of Classification Search
USPC ........................................................ 600/114
See application file for complete search history.

(56) References Cited

U.S. PATENT DOCUMENTS

| | | | |
|---|---|---|---|
| 2004/0019254 A1* | 1/2004 | Belson ................... | A61B 1/018 600/146 |
| 2012/0302831 A1* | 11/2012 | Ashida ............... | A61B 1/00135 600/114 |
| 2014/0296771 A1* | 10/2014 | Naito ................. | G02B 23/2476 604/19 |
| 2014/0298932 A1 | 10/2014 | Okamoto | |
| 2015/0196191 A1* | 7/2015 | Naito ................. | A61B 1/00156 600/114 |
| 2016/0150945 A1 | 6/2016 | Okamoto | |
| 2016/0249787 A1 | 9/2016 | Miyoshi | |

FOREIGN PATENT DOCUMENTS

| | | |
|---|---|---|
| JP | H07-222749 A | 8/1995 |
| JP | 4965002 B2 | 7/2012 |
| JP | 5458224 B1 | 4/2014 |
| JP | 2014-223293 A | 12/2014 |
| JP | 5750622 B1 | 7/2015 |
| WO | WO 2014/084135 A1 | 6/2014 |
| WO | WO 2015/072233 A1 | 5/2015 |

* cited by examiner ately caused to perform a bending movement by an operation of the bending operation knob.

INSERTION DEVICE HAVING UNIVERSAL CORD WITH EXTENDING TRANSMISSION MEMBER

CROSS REFERENCE TO RELATED APPLICATION

This application is a continuation application of PCT/JP2016/076834 filed on Sep. 12, 2016 and claims benefit of Japanese Application No. 2015-212020 filed in Japan on Oct. 28, 2015, the entire contents of which are incorporated herein by this reference.

BACKGROUND OF THE INVENTION

Field of the Invention

The present invention relates to an insertion device including a drive source and a driven member disposed inside a flexible tube, and a transmission member provided inside the flexible tube along a long axis to transmit a rotational driving force of the drive source to the driven member.

Description of the Related Art

Endoscopes are used in medical and industrial fields, for example.

A medical endoscope enables observation, examination, treatment or the like by having an insertion section inserted inside a body which is an examination part.

An endoscope generally includes an insertion section, an operation section, and a universal cord. With a configuration where the insertion section includes a flexible tube section, the insertion section is inserted into a digestive organ/digestive tract through an anus, a mouth, or a nose.

Japanese Patent No. 4965002 discloses an electronic endoscope including an elongated insertion section to be inserted into a body or the like, an operation section provided at a proximal end of the insertion section, and a universal cord extending from a side portion of the operation section.

The flexible tube section of the insertion section and the universal cord of the electronic endoscope are each configured by including a flexible coiled tube, and for example, a coiled tube configuring the universal cord is a layered tube member stacking an envelope, a mesh tube, and a helical tube, and includes a through hole from a distal end to a proximal end. The helical tube is obtained by helically winding a conductive strip-shaped thin metal plate. The mesh tube is a conductive tubular wire mesh formed by weaving conductive metal thin wires into a reticulated pattern and wraps the helical tube. The helical tube and the mesh tube configure a conductive tube member. The envelope is a flexible and insulating resin member. The envelope covers the mesh tube.

Note that a configuration of the coiled tube configuring the flexible tube section is substantially the same as a configuration of the coiled tube of the universal cord, but an outer diameter dimension, a length dimension and the like may be different.

For example, at the time of inserting the insertion section having the flexible tube section configured in the above manner into an intestinal tract, a surgeon inserts the insertion section into a deep region in the intestinal tract by operating a bending operation knob provided on the operation section and bending a bending section, and by performing a twisting operation or a feeding operation of the insertion section positioned outside the body.

However, a great load is applied to a hand or a finger of the surgeon at the time of operation of the bending operation knob. Moreover, the twisting operation or the feeding operation, which is a technique of smoothly inserting the insertion section towards a deep region, requires a high skill.

Accordingly, with respect to the endoscope, electric mechanism sections such as an electric bending mechanism for reducing the load that is applied to a hand or a finger of a surgeon, and an insertion assisting mechanism for moving the insertion section towards or back from a deep region are known.

Japanese Patent No. 5458224 discloses a living body introduction apparatus which corresponds to an external device of the present application and which is provided on a distal side of an insertion section corresponding to a tube body of the present application.

The living body introduction apparatus includes a fin which is formed so as to be wrapped spirally around to function as propulsion site (or a backward site), and a spiral tube provided over an envelope of the insertion section, with a void between the spiral tube and the envelope, to rotate around a longitudinal axis to function as introduction propulsion.

The spiral tube can be rotated by a rotational driving section. A motor, serving as a drive source for the rotational drive section, is disposed in an operation section, and one end of a flexible coil shaft, corresponding to a transmission member of the present application, is coupled to a rotating shaft of the rotational drive section. A rotational force of the motor is transmitted through the flexible coil shaft to rotate a drive gear.

The rotational force of the motor is used to rotate the spiral tube, which is the driven member of the present application, and the insertion section is moved forward by the fin pulling in and compressing a lumen. For example, the spiral tube is made of a flexible material (such as a rubber material or a resin material) or has a flexible structure which enables the spiral tube to follow the bending of the bending section.

Japanese Patent Application Laid-Open Publication No. 2014-223293 discloses an introduction device which is configured to transmit a rotational driving force of a drive section by a torque wire and to operate a functional section, and specifically discloses an electric drive mechanism which is configured to electrically cause a bending function to perform a bending movement.

The electric bending mechanism is configured by mainly including a motor, which is the drive source of the present application, a drive shaft, which is the transmission member of the present application which is a torque wire, and a pulley, which is the driven member of the present application.

The motor generates a rotational driving force for causing a bending section to perform a bending movement. The motor is provided in a first connection section of a drive cable.

The drive shaft transmits a driving force of the motor to the pulley. The drive shaft is covered by a protection tube and is inserted through a universal cord along a long axis.

The pulley bends the bending section upward or downward by being rotated and pulling or loosening an upward bending wire and a downward bending wire. The pulley is provided inside an operation section.

In Japanese Patent Application Laid-Open Publication No. 2014-223293, a pin member is engageably inserted and disposed in a driving force transmission section of a cylindrical member in a state where an output-side case body of a coupling section for output is mounted on a coupling protruding portion provided on a case main body of a coupling section for input by coupling of the first connection section with a drive cable connection section, and a coupled state in which the rotational driving force of the motor can be transmitted to the pulley is thereby achieved.

The pin member is rotated by rotation of a motor shaft 141a of the motor in the coupled state. Then, a first rotation input shaft is rotated, and a first bevel gear is rotated. A second bevel gear is rotated following rotation of the first bevel gear, and a second rotation input shaft is thereby rotated. When the second rotation input shaft is rotated, the drive shaft is rotated, and a rotational driving force of the drive shaft is transmitted to the pulley through a driving force receiving section. As a result, the pulley is rotated to pull an upward wire, for example, and the bending section is bent upward.

Moreover, with the insertion section, of Japanese Patent No. 5458224, provided with the flexible spiral tube capable of following bending of the bending section, the flexibility of the flexible tube section configuring the insertion section is increased with the aim of improving smooth insertability to a deep region. Furthermore, with respect to the universal cord through which the drive shaft of Japanese Patent Application Laid-Open Publication No. 2014-223293 is inserted, the flexibility of the universal cord is increased and the drive shaft is inserted through the universal cord, and thus, the operation section is prevented from becoming difficult to handle.

SUMMARY OF THE INVENTION

An insertion device according to an aspect of the present invention includes a tube body including a coiled tube and extendedly installed in a long axis direction, a drive source disposed on a proximal side of the tube body, a driven member disposed on a distal side of the tube body, and a transmission member provided inside the tube body in a manner extending along a long axis of the tube body, the transmission member being driven to perform rotation around an extension axis by a driving force of the drive source to transmit the rotation to the driven member, where torsional resistance of the tube body around the long axis is set higher than torsional resistance, around the extension axis, of the transmission member extending from an output portion of the drive source to an input portion of the driven member.

DETAILED DESCRIPTION OF THE PREFERRED EMBODIMENT(S)

Figure 1:
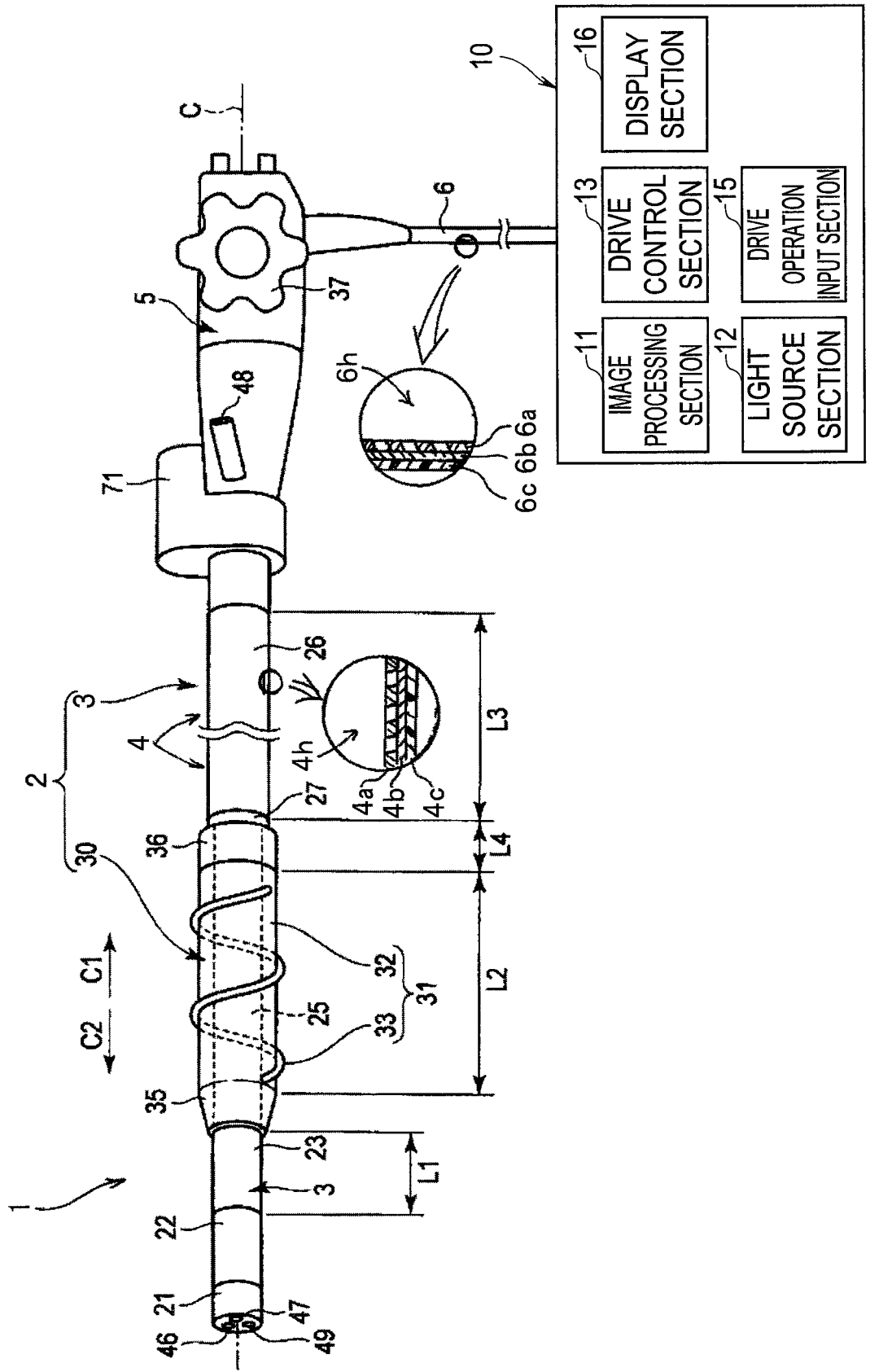
FIG. 1 is a diagram describing an endoscope system including an endoscope according to a first embodiment, where the endoscope is an example of an insertion device and is provided with an insertion assisting mechanism.

Hereinafter, embodiments of the present invention will be described with reference to the drawings.

Note that, in each of the drawings used in the following description, a scale of display may be different for each structural component such that each structural component is large enough to be recognized in the drawing. That is, the present invention is not limited to the modes shown in the drawings with respect to the number of structural components, the shapes of the structural components, the proportion of the sizes of the structural components, and the relative positional relationship of respective structural components.

A first embodiment of the present invention will be described with reference to FIGS. 1 to 6.

In the present embodiment, an insertion appliance is an endoscope 2 shown in FIG. 1. Main sections of an endoscope system 1 include the endoscope 2, and a peripheral unit 10 which is an endoscope external device.

The endoscope 2 of the present embodiment includes an insertion section 3 which is inserted into a body, for example, and the insertion section 3 is provided with a rotary unit 30 as an insertion assisting mechanism, described later, which is an electric mechanism section.

The endoscope 2 includes the insertion section 3 which is extendedly installed along a longitudinal axis C which is a long axis, and an operation section 5 which is provided on a proximal direction side than the insertion section 3.

The insertion section 3 includes a flexible tube section 4 which is a coiled tube and which is a tube body. A proximal end portion of the flexible tube section 4 is connected to the operation section 5. The flexible tube section 4 is a layered tube member stacking a helical tube 4a, a reticular tube 4b, and an envelope 4c in such an order from a center axis side, and has predetermined flexibility. A reference sign 4h is a through hole extending from a distal end to a proximal end of the flexible tube section 4.

The helical tube 4a is formed by helically winding a strip-shaped thin metal plate, for example. The reticular tube 4b is a tubular wire mesh formed by weaving metal thin wires into a reticulated pattern, for example. The reticular tube 4b wraps the helical tube 4a. The envelope 4c is a flexible and insulating resin member. The envelope 4c covers the tubular reticular tube 4b integrating the helical tube 4a and the reticular tube 4b.

One end of a universal cord 6 is connected to the operation section 5. The universal cord 6 is a coiled tube, is a layered tube member stacking a helical tube 6a, a mesh tube 6b, and an envelope 6c in such an order from a center axis side, and has predetermined flexibility. A reference sign 6h is a through hole extending from a distal end to a proximal end of the universal cord 6.

The helical tube 6a, the mesh tube 6b, and the envelope 6c are configured in a substantially same manner as the helical tube 4a, the reticular tube 4b, and the envelope 4c, and outer diameter dimensions, length dimensions, and flexibility of the helical tube 6a, the mesh tube 6b, and the envelope 6c are set as appropriate. In the present embodiment, flexibility is set taking into account the ease of handling of the operation section 5.

The other end of the universal cord 6 is connected to the peripheral unit 10. The peripheral unit 10 includes an image processing section 11, a light source section 12, a drive control section 13, a drive operation input section 15, a display section 16, and the like.

The insertion section 3 includes a distal rigid section 21 forming a distal end of the insertion section 3, a bending section 22 provided on a proximal direction side than the distal rigid section 21, a first flexible tube section 23, a second flexible tube section 25 provided on the proximal direction side than the first flexible tube section 23, and a third flexible tube section 26 provided on the proximal direction side than the second flexible tube section 25, the first flexible tube section 23, the second flexible tube section 25, and the third flexible tube section 26 configuring the flexible tube section 4 provided on the proximal direction side than the bending section 22.

A base section 27 is provided between the second flexible tube section 25 and the third flexible tube section 26, in an axis-parallel direction parallel to the longitudinal axis C. The second flexible tube section 25 is coupled to the third flexible tube section 26 through the base section 27. In the present embodiment, the flexible tube section 4 includes, in such an order from the distal side, the first flexible tube section 23, the second flexible tube section 25, the base section 27, and the third flexible tube section 26.

A first axis-parallel dimension L1 of the first flexible tube section 23 in the axis-parallel direction parallel to the longitudinal axis C is smaller than a second axis-parallel dimension L2 of the second flexible tube section 25 in the axis-parallel direction. Furthermore, the second axis-parallel dimension L2 of the second flexible tube section 25 in the axis-parallel direction is smaller than a third axis-parallel dimension L3 of the third flexible tube section 26 in the axis-parallel direction. Furthermore, a fourth axis-parallel dimension L4 of the base section 27 in the axis-parallel direction is smaller than the first axis-parallel dimension L1.

With reference to a cross section perpendicular to the longitudinal axis C, a direction of moving away from the longitudinal axis C is taken as an outer peripheral direction (a direction away from the axis), and a direction of moving towards the longitudinal axis C is taken as an inner peripheral direction (a direction towards the axis).

A cylindrical rotary unit 30 is provided on an outer peripheral direction side of the insertion section 3. The rotary unit 30 is an external device and is mounted on an outer peripheral surface side of the insertion section 3 with the insertion section 3 inserted through an inside.

The rotary unit 30 mounted on the insertion section 3 rotates relative to the insertion section 3 around the longitudinal axis C when receiving transmission of a rotational driving force in a manner described later.

The rotary unit 30 includes a spiral tube 31 which is extendedly installed along the longitudinal axis C.

The spiral tube 31 includes a corrugated tube portion 32, and a fin portion 33.

The fin portion 33 is provided on an outer peripheral surface of the corrugated tube portion 32, and is extendedly installed, helically around the longitudinal axis C, from a proximal direction to a distal direction of the corrugated tube portion 32.

A distal side cylindrical portion 35 is provided on a distal direction side of the spiral tube 31. The distal side cylindrical portion 35 is tapered with an outer diameter reduced towards the distal direction side. A proximal side cylindrical portion 36 having a cylindrical shape is provided on a proximal direction side of the spiral tube 31.

The rotary unit 30 applies, to the insertion section 3, a propulsion force in a distal direction or a proximal direction by having the spiral tube 31 rotate around the longitudinal axis C in a state where the fin portion 33 is pressed in the inner peripheral direction by a lumen wall or the like.

Mobility of the insertion section 3 in an insertion section inserting direction (distal direction) towards a deep region of a lumen, such as an inner part of a small intestine or an inner part of a large intestine, is increased by a propulsion force in the distal direction, and mobility of the insertion section 3 in an insertion section removal direction (proximal direction) towards outside the lumen is increased by a propulsion force in the proximal direction.

A bending operation knob 37 for causing the bending section 22 to perform a bending movement is provided on an outer surface of the operation section 5. The bending section 22 is bent when bending wires (see reference signs 38A, 38B in FIG. 5) are pulled due to the bending operation knob 37 being operated.

In the present embodiment, the bending section 22 is configured of only an active bending section that bends by a bending operation.

Figure 5:
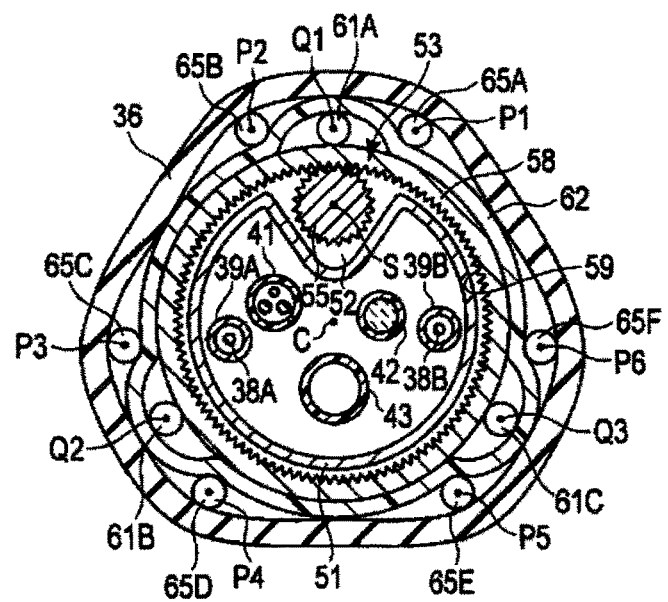
FIG. 5 is a cross-sectional view taken along a line Y5-Y5 in FIG. 4.

Note that the bending wires 38A, 38B are extendedly installed along the longitudinal axis C while being inserted through coils (see reference signs 39A, 39B in FIG. 5). Distal ends of the bending wires 38A, 38B are connected to a distal end portion of the bending section 22, and proximal ends of the bending wires 38A, 38B are connected to a pulley (not shown) coupled to the bending operation knob 37.

Distal ends of the coils 39A, 39B are connected to an inner peripheral surface of a distal end portion of the first flexible tube section 23, and proximal ends of the coils 39A, 39B are extendedly installed in the operation section 5.

In the present embodiment, two bending wires 38A, 38B are provided, and the bending section 22 can be bent in two directions. However, four bending wires may alternatively be provided, for example, so as to enable the bending section 22 to bend in four directions.

Figure 3:
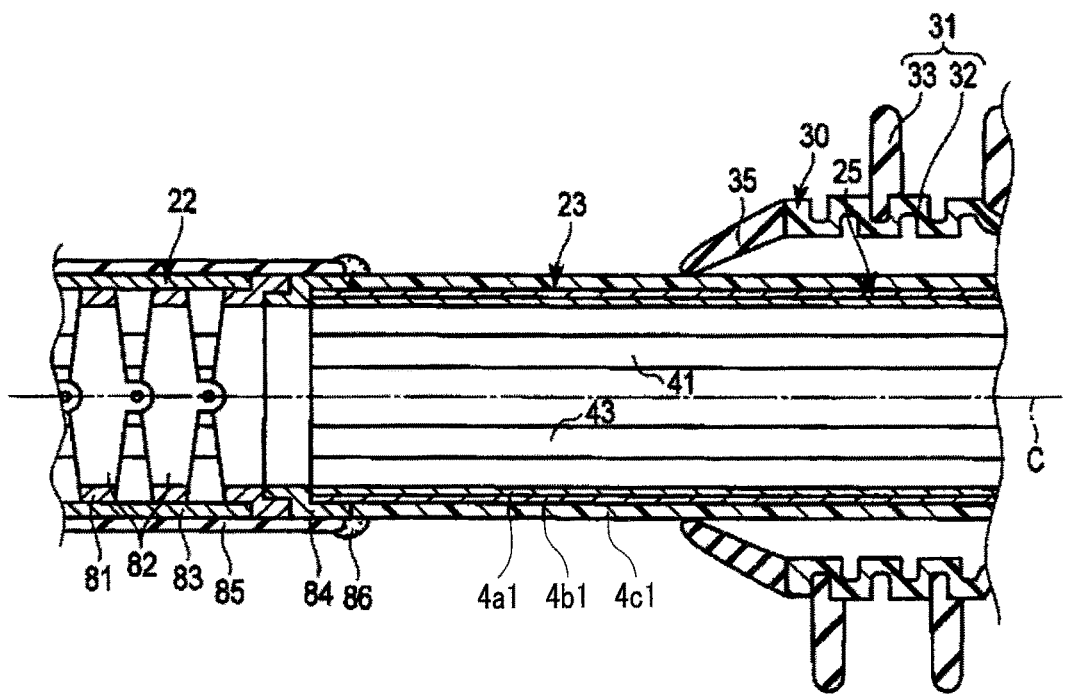
FIG. 3 is a diagram describing an example of configuration of a bending section, a flexible tube section, and the rotary unit according to the first embodiment.
Figure 4:
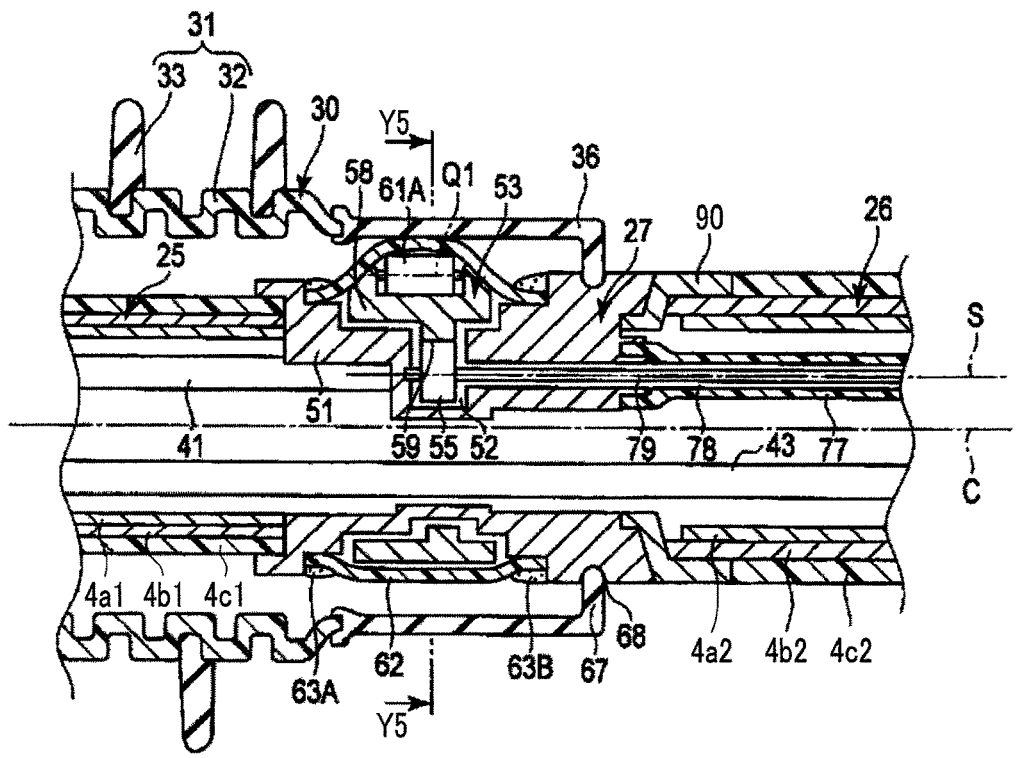
FIG. 4 is a diagram describing the flexible tube section, a base section, and the rotary unit according to the first embodiment.

As shown in FIGS. 3 to 5, an image pickup cable 41, a light guide 42, and a channel tube 43 are extendedly installed along the longitudinal axis C inside the insertion section 3.

An image pickup device (not shown) configured to pick up an image of an object is provided inside the distal rigid section 21 configuring a distal end portion of the insertion section 3. The image pickup device picks up an image of the object through an observation window 46.

One end of the image pickup cable 41 is connected to the image pickup device. The image pickup cable 41 is extendedly installed through inside the insertion section 3, inside the operation section 5, and inside the universal cord 6. The other end of the image pickup cable 41 is connected to the image processing section 11 of the peripheral unit 10. The image processing section 11 performs image processing on a picked-up object image and generates an endoscopic image of the object. The generated endoscopic image of the object is displayed on the display section 16.

The light guide 42 is connected to the light source section 12 of the peripheral unit 10. The light guide 42 is extendedly installed inside the universal cord 6, inside the operation section 5, and inside the insertion section 3. Illumination light emitted from the light source section 12 is guided by the light guide 42 and is radiated towards the object from an illumination window 47 provided in the distal rigid section 21.

A reference sign 48 in FIG. 1 is a treatment instrument insertion section. The treatment instrument insertion section 48 includes an insertion port where a treatment instrument, such as forceps, is to be inserted, and is provided on the outer surface of the operation section 5. The channel tube 43 shown in FIGS. 3 to 5 has one end connected to the treatment instrument insertion section 48, and is extendedly installed through inside the operation section 5, and inside the insertion section 3. A treatment instrument inserted from the treatment instrument insertion section 48 passes through inside of the channel tube 43 and is guided to outside from an opening portion 49 formed in the distal rigid section 21.

As shown in FIG. 4, a support member 51 formed of metal is provided at the base section 27. A proximal end portion of the second flexible tube section 25 is coupled to a distal end portion of the support member 51, and a distal end portion of the third flexible tube section 26 is coupled to a proximal end portion of the support member 51 through a connection member 90. The second flexible tube section 25 and the third flexible tube section 26 are thereby connected to each other through the base section 27.

As shown in FIGS. 4 and 5, a hollow portion 52 is defined in the base section 27 by the support member 51. Furthermore, a driving force transmission unit 53 as a driven member is attached to the support member 51. The driving force transmission unit 53 is disposed in the hollow portion 52.

The driving force transmission unit 53 is driven when receiving transmission of a rotational driving force for rotating the rotary unit 30. The driving force transmission unit 53 includes a drive gear 55.

The driving force transmission unit 53 includes a rotary cylindrical member 58. The rotary cylindrical member 58 is rotatably engaged with the base section 27 in a state where the support member 51 is inserted through the rotary cylindrical member 58. The rotary cylindrical member 58 is capable of rotating relative to the insertion section 3 (base section 27) around the longitudinal axis C.

Two directions in which the rotary unit 30 rotates is given as a longitudinal axis circumferential direction.

An inner peripheral gear portion 59 is provided on an inner peripheral surface of the rotary cylindrical member 58, around an entire circumference in the longitudinal axis circumferential direction. The drive gear 55 is meshed with the inner peripheral gear portion 59.

In the present embodiment, three inner rollers 61A, 61B, 61C are attached to the rotary cylindrical member 58. The inner rollers 61A, 61B, 61C are disposed separated from one another at a substantially equal distance in the longitudinal axis circumferential direction. The inner rollers 61A, 6B, 61C include corresponding roller shafts Q1, Q2, Q3, respectively.

Each inner roller 61A, 61B, 61C is capable of rotating relative to the rotary cylindrical member 58 around the corresponding roller shaft Q1, Q2, Q3. Moreover, the inner rollers 61A, 61B, 61C are capable of rotating relative to the insertion section 3 (base section 27) around the longitudinal axis C, in an integrated manner with the rotary cylindrical member 58.

The rotary cylindrical member 58 and the inner rollers 61A, 61B, 61C are covered by a cylindrical cover member 62 on an outer peripheral direction side. A distal end of the cover member 62 is fixed to an outer peripheral surface of the support member 51 by an adhesive portion 63A such as an adhesive, and a proximal end of the cover member 62 is fixed to the outer peripheral surface of the support member 51 by an adhesive portion 63B such as an adhesive.

The hollow portion 52 where the driving force transmission unit 53 is disposed is partitioned from outside the insertion section 3 by the cover member 62. Liquid-tightness is maintained between the support member 51 and the cover member 62, at a fixation position at a distal end of the cover member 62 and a fixation position at a proximal end of the cover member 62.

Accordingly, liquid is prevented from flowing into the hollow portion 52 and the driving force transmission unit 53 from outside the insertion section 3. Moreover, at portions in the longitudinal axis circumferential direction where the inner rollers 61A, 61B, 61C are positioned, the cover member 62 protrudes in an outer peripheral direction.

Note that the cover member 62 is fixed to the insertion section 3, and the rotary cylindrical member 58 and the inner rollers 61A, 61B, 61C are capable of rotating relative to the cover member 62 in the longitudinal axis circumferential direction.

As shown in FIG. 5, six outer rollers 65A, 65B, 65C, 65D, 65E, 65F (hereinafter referred to also as "outer rollers 65A-65F") are attached on an inner peripheral surface of the proximal side cylindrical portion 36. The outer rollers 65A-65F are positioned on an outer peripheral direction side of the cover member 62.

In a state where the rotary unit 30 is mounted on the insertion section 3, the inner roller 61A is positioned between the outer roller 65A and the outer roller 65B in the longitudinal axis circumferential direction, and the inner roller 61B is positioned between the outer roller 65C and the outer roller 65D in the longitudinal axis circumferential direction. Furthermore, the inner roller 61C is positioned between the outer roller 65E and the outer roller 65F in the longitudinal axis circumferential direction.

The outer rollers 65A-65F include roller shafts P1, P2, P3, P4, P5, P6 (hereinafter referred to also as "roller shafts P1-P6"), respectively. Each outer roller 65A-65F is capable of rotating relative to the cover member 62 and the proximal side cylindrical portion 36 around the corresponding roller shaft P1-P6. Moreover, the outer rollers 65A-65F are capable of rotating relative to the insertion section 3 (base section 27) around the longitudinal axis C, in an integrated manner with the rotary unit 30.

When the driving force transmission unit 53 is driven by a rotational driving force, the rotary cylindrical member 58 rotates around the longitudinal axis C. The inner roller 61A then presses the outer roller 65A or the outer roller 65B.

In the same manner, the inner roller 61B presses the outer roller 65C or the outer roller 65D, and the inner roller 61C presses the outer roller 65E or the outer roller 65F. A driving force is thereby transmitted from the inner rollers 61A, 61B, 61C to the outer rollers 65A-65F of the rotary unit 30, and the rotary unit 30 rotates relative to the insertion section 3 and the cover member 62 around the longitudinal axis C.

The outer rollers 65A-65F attached to the proximal side cylindrical portion 36 in the manner described above are driving force receiving portions for receiving a rotational driving force from the driving force transmission unit 53 which is driven. The outer rollers 65A-65F as the driving force receiving portions are provided on the proximal direction side than the spiral tube 31. Moreover, in a state where the rotary unit 30 is mounted on the insertion section 3, the outer rollers 65A-65F are positioned on an outer peripheral direction side of the base section 27.

Note that each of the inner rollers 61A, 61B, 61C rotates around the corresponding roller shaft Q1, Q2, Q3. Accordingly, friction between each inner roller 61A, 61B, 61C and the cover member 62 is reduced.

Moreover, each of the outer rollers 65A-65F rotates around the corresponding roller shaft P1-P6 in the same manner. Accordingly, friction between each outer roller 65A-65F and the cover member 62 is also reduced.

Therefore, a rotational driving force is appropriately transmitted from the inner rollers 61A, 61B, 61C to the rotary unit 30, and the rotary unit 30 is appropriately rotated.

An engaging claw 67 protruding in the inner peripheral direction is provided at the proximal side cylindrical portion 36. Furthermore, an engaging groove 68 is provided at the support member 51 of the base section 27, around an entire circumference in the longitudinal axis circumferential direction. Movement of the rotary unit 30 along the longitudinal axis C of the insertion section 3 is restricted by the engagement of the engaging claw 67 with the engaging groove 68.

Note that an amount of relative movement is set greater than an amount of slack in a long axis direction caused by rotation of a drive shaft 79 described later.

In a state where the engaging claw 67 is engaged with the engaging groove 68, the engaging claw 67 is capable of moving relative to the engaging groove 68 in the longitudinal axis circumferential direction.

Figure 2:
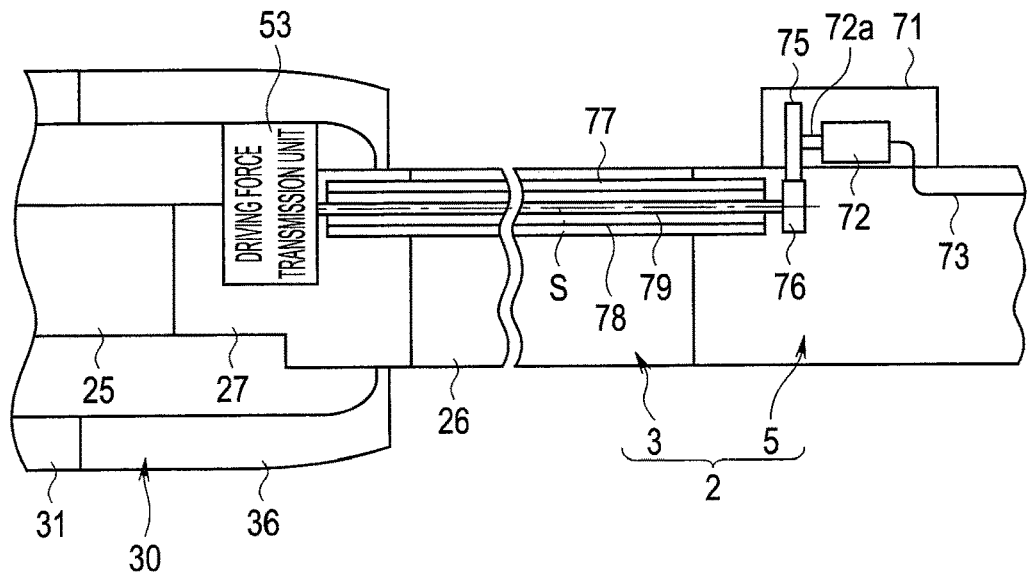
FIG. 2 is a diagram describing a configuration for transmitting a rotational driving force to a rotary unit according to the first embodiment.

As shown in FIGS. 1 and 2, a motor housing 71 is fixedly installed at the operation section 5. A motor 72 as a drive source is housed inside the motor housing 71 and is fixed to the housing 71 in an integrated manner. One end of a motor cable 73 is connected to the motor 72, and the other end is connected to the drive control section 13 of the peripheral unit 10. Moreover, the motor cable 73 is extendedly installed through inside the operation section 5, and inside the universal cord 6.

When power is supplied from the drive control section 13 to the motor 72 through the motor cable 73, a shaft portion 72a of the motor 72 is driven clockwise or counterclockwise. When the motor 72 is driven, a rotational driving force for rotating the rotary unit 30 is generated.

A relay gear 75 as an output portion is attached to the shaft portion 72a of the motor 72. Furthermore, a drive gear 76 which is meshed with the relay gear 75 is provided inside the operation section 5. The relay gear 75 and the drive gear 76 configure a reduction gear mechanism.

As shown in FIGS. 2 and 4, inside the third flexible tube section 26 of the insertion section 3, a guide tube 77 having a through hole along an axis direction is extendedly installed along the longitudinal axis C. A distal end of the guide tube 77 is connected to the support member 51 of the base section 27. A distal side of a guide channel 78 communicates with the hollow portion 52. The guide tube 77 is a protection member, and the through hole along the axis direction is formed as the guide channel 78.

The drive shaft 79 as a transmission member is inserted through and disposed in the guide channel 78. A shaft axis S of the drive shaft 79 is extendedly installed along the longitudinal axis C. The drive shaft 79 is a flexible shaft, a torque coil, which is a multi-threaded, multi-layered coil, or a torque wire, for example, and in the present embodiment, the drive shaft 79 is, for example, a multi-threaded, multi-layered coil having two coil layers, and is formed by spirally winding special hard steel wires or stainless steel wires for spring clockwise and counterclockwise alternately around the shaft axis S to form several layers.

Moreover, the drive shaft 79 is formed of a wire rod of a wire diameter selected in advance, and torsional resistance (also referred to as "torsional rigidity") is set to achieve predetermined torsional characteristics at the time of rotation in a winding direction.

A rotational driving force of the motor 72 is transmitted to the drive shaft 79 through the relay gear 75 and the drive gear 76. The drive shaft 79 rotates around the shaft axis S when the rotational driving force is transmitted to the drive shaft 79.

A distal end of the drive shaft 79 is connected to the drive gear 55 of the driving force transmission unit 53 as an input portion. Rotation of the drive shaft 79 around the axis is transmitted to the driving force transmission unit 53, and the driving force transmission unit 53 is thereby driven. Then, the rotational driving force transmitted to the driving force transmission unit 53 is transmitted to the rotary cylindrical member 58, and thus, the rotational driving force is transmitted to rotate the rotary unit 30 as described above.

As shown in FIGS. 1, 3 and 4, in the present embodiment, the first flexible tube section 23 and the second flexible tube section 25 are formed of a first helical tube 4a1, a first flexible reticular tube 4b1, and a first flexible envelope 4c1. The first helical tube 4a1, the first flexible reticular tube 4b1, and the first flexible envelope 4c1 are extendedly installed along the longitudinal axis C, from a distal end of the first flexible tube section 23 to a proximal end of the second flexible tube section 25.

As shown in FIG. 3, the bending section 22 includes a bending tube 81. The bending tube 81 includes a plurality of metal bending pieces 82. Each bending piece 82 is rotatably coupled to an adjacent bending piece 82. At the bending section 22, a bending reticular tube 83 as a bending blade covers an outer peripheral direction side of the bending tube 81. The bending reticular tube 83 is formed by weaving metal wires (not shown) into a reticulated pattern. Furthermore, at the bending section 22, a bending envelope 85 covers an outer peripheral direction side of the bending reticular tube 83. For example, the bending envelope 85 is formed of fluorine rubber.

A proximal end portion of the bending tube 81 is fitted with a cylindrical connection tube 84. The first helical tube 4a1 and the first flexible reticular tube 4b1 are fitted with the connection tube 84 while being inserted on an inner peripheral direction side of the connection tube 84. Furthermore, the first flexible envelope 4c1 is bonded to the bending envelope 85 by an adhesive portion 86 such as an adhesive. The first flexible tube section 23 and the bending section 22 are coupled to each other in the above manner.

As shown in FIGS. 4 and 5, the first helical tube 4a1, the first flexible reticular tube 4b1, and the first flexible envelope 4c1 are fitted with the support member 51 while being inserted on an inner peripheral direction side of the support member 51. The second flexible tube section 25 is thereby coupled to the base section 27. Furthermore, in the present embodiment, the first helical tube 4a1, the first flexible reticular tube 4b1, and the first flexible envelope 4c1 are extendedly installed between the first flexible tube section 23 and the second flexible tube section 25 in a continuous manner.

Figure 6:
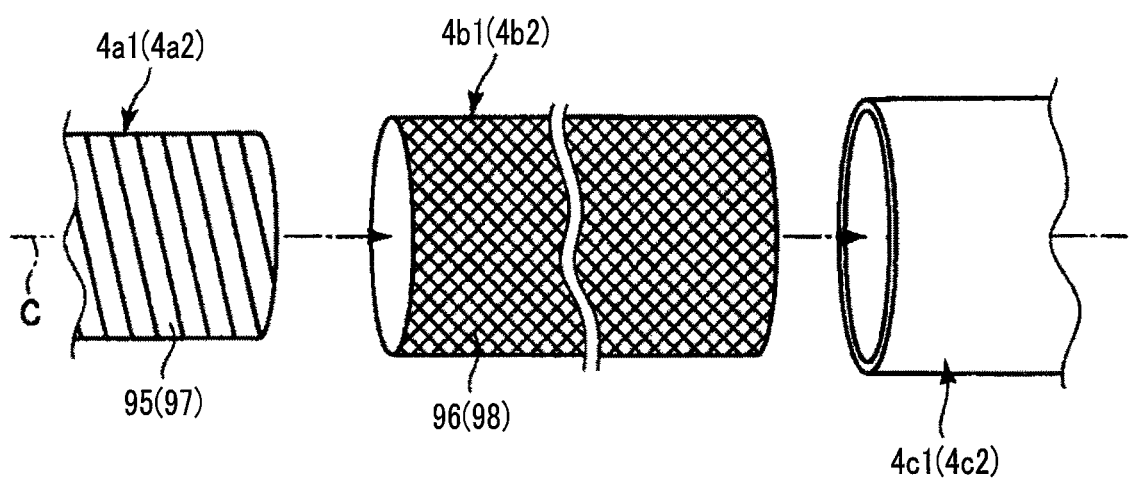
FIG. 6 is a diagram describing an example of a configuration of a flexible tube according to the first embodiment.

As shown in FIG. 6, the first helical tube 4a1 includes a strip-shaped member 95 of metal, and the strip-shaped member 95 is extendedly installed while being helically wound around the longitudinal axis C. The first flexible reticular tube 4b1 includes a metal wire 96 which is woven. The first flexible envelope 4c1 is formed of a resin material.

The third flexible tube section 26 shown in FIG. 4 is formed of a second helical tube 4a2, a second flexible reticular tube 4b2, and a second flexible envelope 4c2 shown in FIG. 6. The second helical tube 4a2, the second flexible reticular tube 4b2, and the second flexible envelope 4c2 are extendedly installed along the longitudinal axis C, from a distal end of the third flexible tube section 26 to a proximal end of the third flexible tube section 26.

The proximal end portion of the support member 51 is fitted with the connection member 90. The second helical tube 4a2 and the second flexible reticular tube 4b2 are fitted with the connection member 90 while being inserted on an inner peripheral direction side of the connection member 904. The third flexible tube section 26 is thereby coupled to the base section 27.

As shown in FIG. 6, at the second helical tube 4a2, a strip-shaped member 97 of metal is extendedly installed while being helically wound around the longitudinal axis C. At the second flexible reticular tube 4b2, a metal wire 98 is woven. The second flexible envelope 4c2 is formed of a resin material.

Note that, in FIG. 6, structures related to the first flexible tube section 23 and the second flexible tube section 25 are indicated by reference signs without parentheses, and structures related to the third flexible tube section 26 are indicated by reference signs in parentheses.

As described above, the outer rollers 65A-65F, which are driving force receiving portions of the rotary unit 30 mounted on the insertion section 3, are positioned on the outer peripheral direction side of the base section 27. That is, a proximal end of the rotary unit 30 is disposed on the outer peripheral direction side of the base section 27. The rotary unit 30 is extendedly installed towards the distal direction from the position on the outer peripheral direction side of the base section 27.

Accordingly, the rotary unit 30 mounted on the insertion section 3 does not cover an outer peripheral direction side of the third flexible tube section 26. In other words, in a state where the rotary unit 30 is mounted on the insertion section 3, the spiral tube 31 covers an outer peripheral direction side of the second flexible tube section 25.

Moreover, a distal end of the rotary unit 30 is positioned at a region between the first flexible tube section 23 and the second flexible tube section 25 in the axis-parallel direction parallel to the longitudinal axis C. Accordingly, in the state where the rotary unit 30 is mounted on the insertion section 3, an outer peripheral direction side of the first flexible tube section 23 is not covered by the rotary unit 30.

The bending section 22 includes the bending tube 81 configured to bend along an axis orthogonal to the longitudinal axis C, and the bending envelope 85 is formed of a highly flexible material. Moreover, the bending section 22 is set to have higher flexibility than any of the first flexible tube section 23, the second flexible tube section 25, and the third flexible tube section 26.

Furthermore, the spiral tube 31 of the rotary unit 30 is formed of a highly flexible resin and is set to have higher flexibility than any of the first flexible tube section 23, the second flexible tube section 25, and the third flexible tube section 26.

Note that the first flexible tube section 23, the second flexible tube section 25, and the third flexible tube section 26 are each variable depending on an inner diameter of the helical tube 4a1, 4a2, a thickness of the strip-shaped member 95, 97, the number of layers of the helical tube 4a1, 4a2, a diameter of the wire 96,98 of the flexible reticular tube 4b1, 4b2, a thickness of the flexible envelope 4c1, 4c2, an outer diameter of the flexible tube section 23, 25, 26, hardness of resin forming the flexible envelope 4c1, 4c2, and the like.

More specifically, the flexibility of the flexible tube section 23, 25, 26 is more reduced as the inner diameter of the helical tube 4a1, 4a2 is increased, or as the thickness of the strip-shaped member 95, 97 is increased, or as the number of layers of the helical tube 4a1, 4a2 is increased, or as the diameter of the wire 96, 98 is increased, or as the thickness of the flexible envelope 4c1, 4c2 is increased. Furthermore, if the hardness of resin forming the flexible envelope 4c1, 4c2 is increased, the flexibility of the flexible tube section 23, 25, 26 is reduced.

Moreover, in a state where the rotary unit 30 is not mounted on the insertion section 3, the first flexible tube section 23 is highly likely to have the same flexibility as the second flexible tube section 25, or higher flexibility than the flexibility of the first flexible tube section 23. In the present embodiment, for example, the first flexible tube section 23 is caused to have different flexibility from the second flexible tube section 25 by changing the hardness of resin of the first flexible envelope 4c1 between the first flexible tube section 23 and the second flexible tube section 25.

Note that, in the present embodiment, in any of cases including the examples described above, the second flexible tube section 25 has the same or higher flexibility than the first flexible tube section 23 in a state where the spiral tube 31 is not disposed covering the second flexible tube section 25.

However, even in the case where the second flexible tube section 25 is not covered by the spiral tube 31, the second flexible tube section 25 has lower flexibility than the spiral tube 31 and the bending section 22.

Furthermore, in a state where the spiral tube 31 covers the outer peripheral direction side of the second flexible tube section 25, the flexibility at the part of the second flexible tube section 25 is lower than the flexibility of the first flexible tube section 23.

However, the spiral tube 31 has higher flexibility than the first flexible tube section 23 and the second flexible tube section 25. The second flexible tube section 25 has the same or higher flexibility than the first flexible tube section 23. Accordingly, even in a state where the second flexible tube section 25 is covered by the spiral tube 31, the flexibility of the second flexible tube section 25 does not become excessively lower than the flexibility of the first flexible tube section 23.

The flexibility of the third flexible tube section 26 is lower than the flexibilities of the first flexible tube section 23 and the second flexible tube section 25 across an entire length in the axis-parallel direction parallel to the longitudinal axis C.

Inside the insertion section 3, the guide tube 77 and the drive shaft 79 are extendedly installed towards the distal direction up to the hollow portion 52 defined by the support member 51. That is, the guide tube 77 and the drive shaft 79, which are not extendedly installed inside the first flexible tube section 23 and the second flexible tube section 25, are extendedly installed inside the third flexible tube section 26.

Accordingly, the number of internal components embedded in the third flexible tube section 26 is greater compared to the number of internal components embedded in each of the first flexible tube section 23 and the second flexible tube section 25. Furthermore, because the number of internal components is great, a cross-sectional area of a space formed inside the third flexible tube section 26, which is perpendicular to the longitudinal axis C has to be greater than perpendicular cross-sectional areas of the first flexible tube section 23 and the second flexible tube section 25.

Accordingly, the inner diameter of the second helical tube 4a2 of the third flexible tube section 26 has to be made greater than the inner diameter of the first helical tube 4a1 configuring the first flexible tube section 23 and the second flexible tube section 25, and thus, the flexibility of the third flexible tube section 26 is reduced compared to the first flexible tube section 23 and the second flexible tube section 25.

In addition, in the present embodiment, torsional rigidity of the third flexible tube section 26 is set higher than torsional rigidity of the drive shaft 79 disposed inside the guide channel 78. That is, with respect to the third flexible tube section 26, the thickness of the strip-shaped member 97, the diameter of the wire, the thickness of the flexible envelope 4c2, or the hardness of resin is set as appropriate, and the torsional rigidity is set higher than the torsional rigidity of the drive shaft 79, and the flexibility is set lower than the flexibilities of the first flexible tube section 23 and the second flexible tube section 25.

Effects of the endoscope 2 configured in the above manner will now be described.

For example, at the time of inserting the insertion section 3 into an intestinal tract, a surgeon inserts the insertion section 3 by holding the operation section 5 of the endoscope 2 with the left hand, and the flexible tube section 4 with the right hand. Then, the surgeon inserts the insertion section 3 towards a deep region by rotating the spiral tube 31 of the rotary unit 30 and obtaining a propulsion force for moving the insertion section 3 in the distal direction as necessary, for example.

When the surgeon selects driving of the motor 72 so as to rotate the rotary unit 30, the shaft portion 72a of the motor 72 starts rotating, and rotation of the shaft portion 72a is transmitted to the drive gear 76 meshed with the relay gear 75 attached to the shaft portion 72a. Then, rotation of the drive gear 76 is transmitted to the drive shaft 79 connected to the gear 76, and the shaft 79 rotates around the shaft axis S.

Rotation of the drive shaft 79 around the axis is transmitted to the rotary cylindrical member 58 through the inner peripheral gear portion 59 meshed with the drive gear 55, and the rotary cylindrical member 58 starts rotating. Then, as described above, the driving force is transmitted from the inner rollers 61A, 61B, 61C to the outer rollers 65A-65F of the rotary unit 30, and the proximal side cylindrical portion 36 is rotated, and the rotary unit 30 rotates relative to the insertion section 3 and the cover member 62 around the longitudinal axis C. As a result, a propulsion force for moving the insertion section 3 in the distal direction is obtained from the rotary unit 30.

When the insertion section 3 is moved in the intestinal tract towards a deep region while obtaining a propulsion force, the second flexible tube section 25 to which the rotary unit 30 is mounted possibly passes through a bent portion of the intestinal tract or a narrowed portion where the lumen is narrowed, for example.

At the time of the insertion section 3 passing through a bent portion of the intestinal tract, the spiral tube 31 and the second flexible tube section 25 are deformed, thereby increasing a frictional force between the first flexible envelope 4c1 of the second flexible tube section 25 and the corrugated tube portion 32, and increasing a frictional force between the distal side cylindrical portion 35 and the first flexible envelope 4c1 of the first flexible tube section 23.

At the time of the insertion section 3 passing through a narrowed portion, the spiral tube 31 is deformed due to an external force from an intestinal wall, thereby increasing a frictional force between the distal side cylindrical portion 35 and the first flexible envelope 4c1 of the first flexible tube section 23, and also, possibly increasing a frictional force between the corrugated tube portion 32 and the first flexible envelope 4c1 of the second flexible tube section 25.

An increase in a frictional force as mentioned above prevents the spiral tube 31 from rotating, and thus, a propulsion force becomes difficult to obtain. In such an instance, for example, the surgeon stops driving of the motor 72 or causes the shaft portion 72a of the motor 72 to rotate in an opposite direction upon determining, based on an endoscopic image displayed on the display section 16, that a propulsion force is not obtained.

Here, if the surgeon does not notice that a propulsion force is not obtained, the shaft portion 72a of the motor 72 keeps rotating. However, because rotation of the spiral tube 31 is disabled, rotation of the relay gear 75 is not transmitted to the drive gear 76, that is, the drive shaft 79 is not rotated, by rotation of the shaft portion 72a.

Accordingly, a torsional force is applied to the drive shaft 79 while the relay gear 75 is rotating according to rotation of the shaft portion 72a. On the other hand, while the drive shaft 79 is prevented from rotating, an external force acts to cause the relay gear 75 to revolve around the drive gear 75. However, because the motor 72 is integrally fixed to the housing 71, the relay gear 75 does not revolve, and the external force is transmitted to the motor 72 through the shaft portion 72 to which the relay gear 75 is attached.

Then, the external force transmitted to the motor 72 acts as a torsional force on the housing 71 fixedly installed on the operation section 5. Because the housing 71 is fixedly installed on the operation section 5, the torsional force acts as a torsional force for twisting the operation section 5. As a result, the torsional force transmitted to the operation section 5 acts on the flexible tube section 4 connected to the operation section 5.

As described above, the flexible tube section 4 is configured by including the first flexible tube section 23, the second flexible tube section 25, the base section 27, and the third flexible tube section 26 in such an order from the distal side. Furthermore, the frictional force between the first flexible envelope 4c1 of the second flexible tube section 25 and the corrugated tube portion 32, and the frictional force between the distal side cylindrical member 35 and the first flexible envelope 4c1 of the first flexible tube section 23 are increased. Accordingly, the third flexible tube section 23, 26 positioned on a proximal side of the base section 27 is twisted due to application of the torsional force.

In the present embodiment, the torsional rigidity of the third flexible tube section 26 is set higher than the torsional rigidity of the drive shaft 79. As a result, the third flexible tube section 26 may be reliably prevented from being damaged before the drive shaft 79, in a state where the frictional force between the first flexible envelope 4c1 of the second flexible tube section 25 and the corrugated tube portion 32 and the frictional force between the distal side cylindrical portion 35 and the first flexible envelope 4c1 of the first flexible tube section 23 are increased, rotation of the spiral tube 31 is stopped, and a torsional force is applied to the third flexible tube section 26.

Accordingly, a situation where the endoscope 2 provided with the rotary unit 30 as the insertion assisting mechanism has to be repaired due to the third flexible tube section 26 being damaged before the drive shaft 79 is prevented.

A second embodiment of the present invention will be described with reference to FIGS. 7 to 10.

Figure 7:
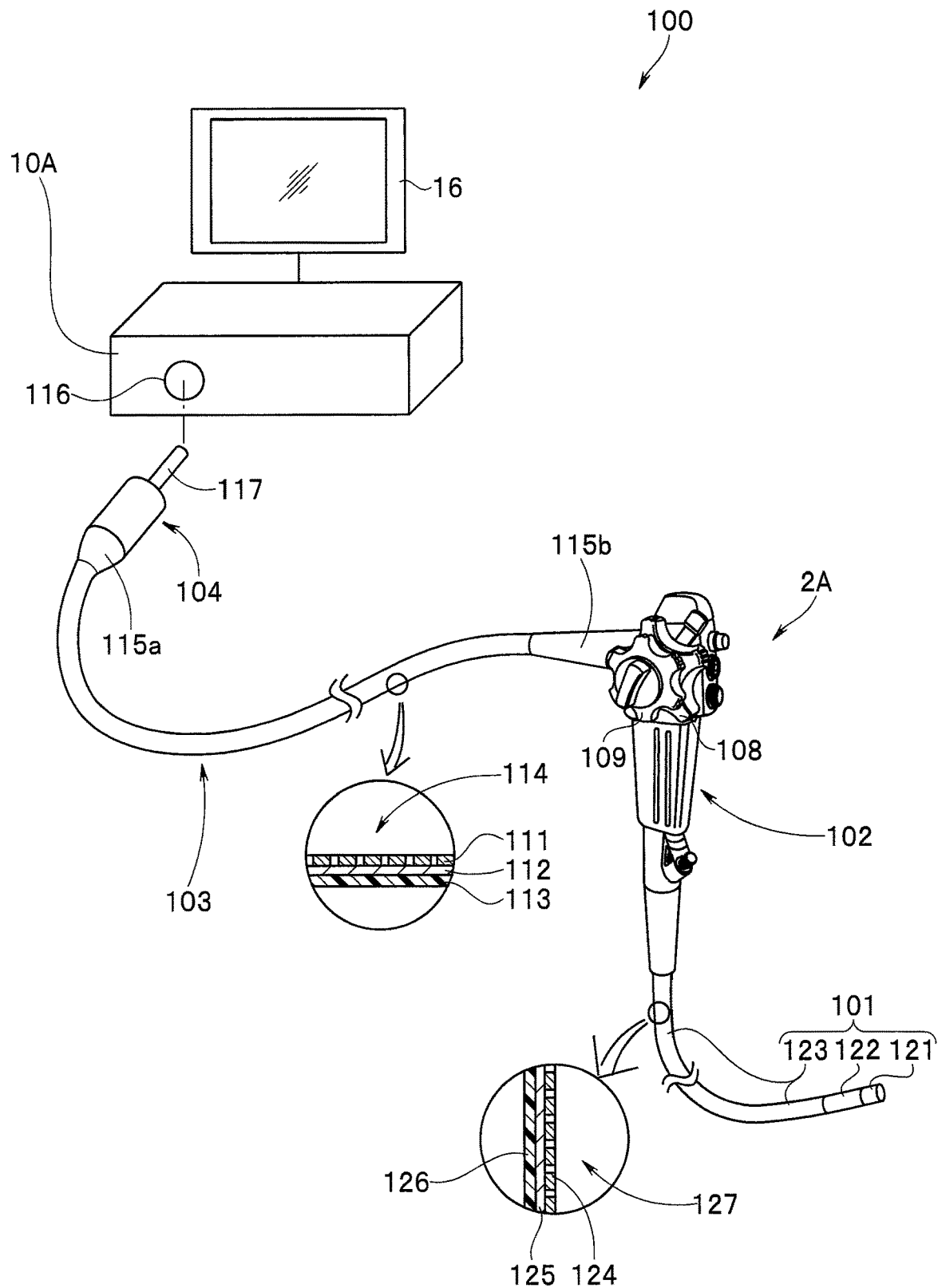
FIG. 7 is a diagram describing an endoscope system including an endoscope according to a second embodiment, where the endoscope is another example of the insertion device and is provided with an electric bending mechanism.

As shown in FIG. 7, an introduction device according to the present embodiment is an endoscope 2A. Main sections of an endoscope system 100 include the endoscope 2A, and a peripheral unit 10A. In the present embodiment, the image processing section, the light source section, the drive control section, and the drive operation input section described above are provided in the peripheral unit 10A. A reference sign 16 is the display section where an endoscopic image is displayed as described above.

The endoscope 2A of the present embodiment is provided with an electric bending mechanism as an insertion assisting mechanism, described later, which is an electric mechanism section.

The endoscope 2A includes an elongated insertion section 101 which is inserted into a body, for example. An operation section 102 is provided on a proximal side of the insertion section 101. A flexible universal cord 103 extends from the operation section 102. A connector 104 is provided on an extended end of the universal cord 103.

The universal cord 103 is a tube body, is a coiled tube as described above, and is a layered tube member stacking a helical tube 111, a mesh tube 112, and an envelope 113 in such an order from a center axis side. The universal cord 103 has predetermined flexibility with a thickness of a strip-shaped member, a diameter of a wire, a thickness of the flexible envelope 113, or hardness of resin set as appropriate taking into account the ease of handling of the operation section 102. A reference sign 114 is a through hole extending from a distal end to a proximal end of the universal cord 103.

Reference signs 115a, 115b are bend preventing tubes which prevent buckling of the universal cord 103 integrally fixed to a connector main body (reference sign 130 in FIGS. 8 and 9) described later, and buckling of the universal cord 103 integrally fixed to an operation section main body (reference sign 150 in FIG. 8) described later. A reference sign 116 is a connector receiver, and the connector 104 can be detachably attached to the connector receiver 116.

The connector 104 is provided with a light guide pipe sleeve 117, a plurality of contact portions (see reference signs 118, 119, 120 in FIG. 8), an air/water feeding pipe sleeve (not shown), and the like.

The insertion section 101 includes a distal end portion 121, a bending section 122, and a flexible tube section 123 which are continuously provided in such an order from a distal side. The bending section 122 is a bending section which bends in four directions of up-down directions and left-right directions. Note that the bending section 122 may alternatively be a bending section that bends in two directions.

The bending section 122 is configured to perform a bending movement when a rotational driving force of a drive motor (see reference sign 141 in FIG. 8) as a drive section is transmitted to a pulley (see reference sign 142 in FIG. 8) as a driven member.

Note that the flexible tube section 123 is a coiled tube, is a layered tube member stacking a helical tube 124, a mesh tube 125, and an envelope 126 in such an order from a center axis side, and is formed to have predetermined flexibility. A reference sign 127 is a through hole extending from a distal end to a proximal end of the flexible tube section 123.

In the present embodiment, the flexible tube section 123 has a substantially same configuration as the first flexible tube section 23 described above. The flexibility of the flexible tube section 123 is set as appropriate.

An up-down bending operation instruction knob 108 and a left-right bending operation instruction knob 109 are provided on the operation section 102 as operation instruction members. The instruction knobs 108, 109 are rotatable around respective axes not shown.

Figure 8:
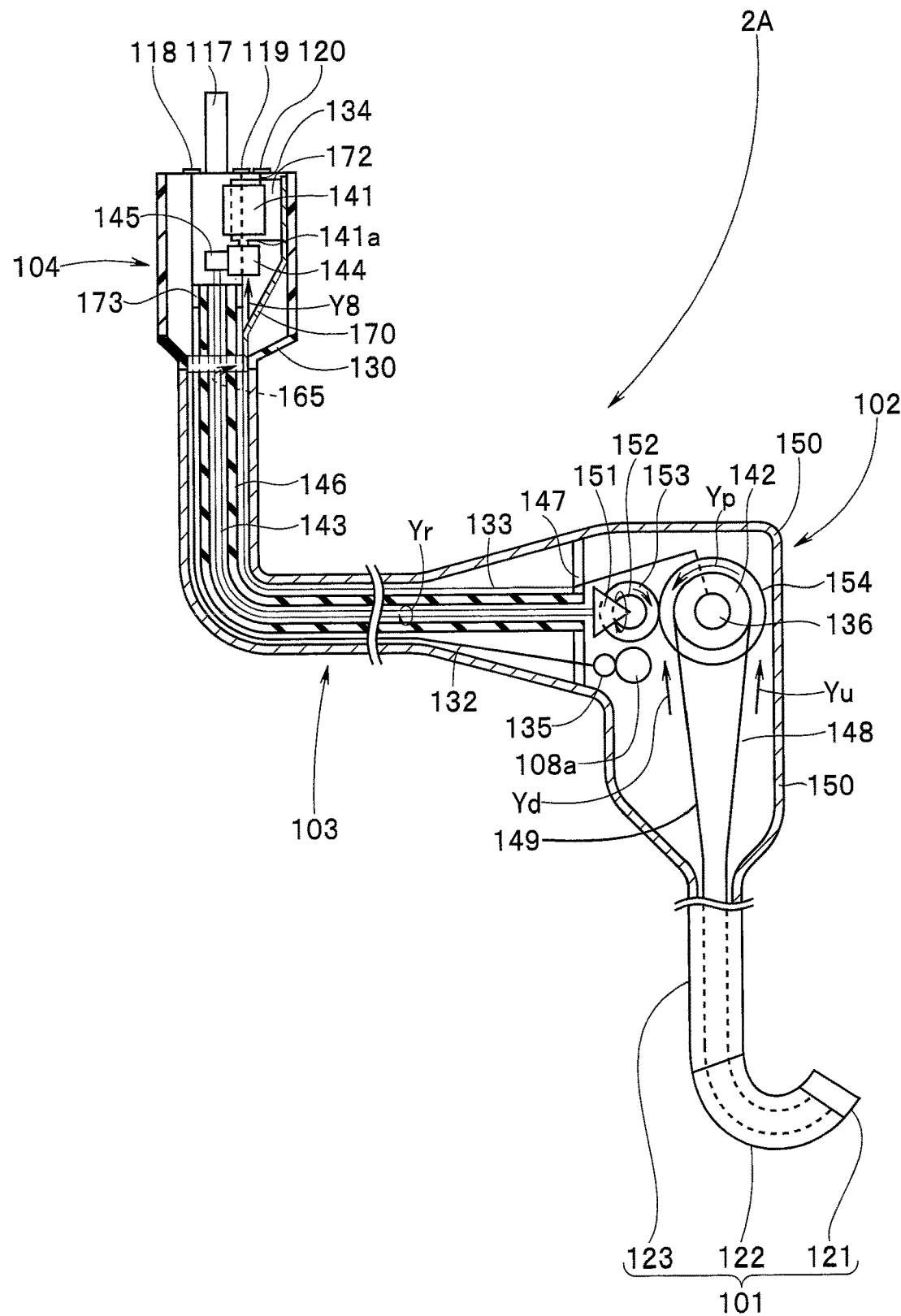
FIG. 8 is a diagram describing a configuration for transmitting a rotational driving force to a pulley according to the second embodiment.

As shown in FIG. 8, the light guide pipe sleeve 117 protrudes from a proximal end surface of the connector main body 130 of the connector 104. Furthermore, the contact portions 118, 119, 120 are provided on the proximal end surface.

The reference sign 141 is a drive motor which is integrally fixed to a motor fixing portion 172 formed to a connector framework part 170 fixedly installed at the connector main body 130. A reference sign 132 is a first signal cable, a reference sign 133 is a second signal cable, and a reference sign 134 is a motor drive cable.

A distal end of the motor drive cable 134 is connected to the drive motor, and a proximal end is connected to the drive control section through the third contact portion 119.

An electric bending mechanism for electrically bending a bending function of the endoscope system 100 will be described with reference to FIG. 8.

Note that, to simplify the drawing, a description will be given, with respect to the bending section 122 in FIG. 8, of a configuration of an electric bending mechanism for electrically driving an up-down bending function while omitting a description of an electric bending mechanism for electrically driving a left-right bending function.

The electric bending mechanism for bending the bending section 122 is mainly configured by including a drive motor (hereinafter abbreviated as "motor") 141 as a drive section, a drive shaft 143 as a transmission member, and a pulley 142.

The motor 141 generates a driving force for causing the bending section 122 to perform a bending movement. The motor 141 is driven by power and a control signal outputted from the drive control section. An encoder for motor (not shown) for detecting rotation of a motor shaft 141a is provided at the motor 141.

The motor shaft 141a of the motor 141 is capable of rotating clockwise or counterclockwise. An amount of rotation of the motor shaft 141a is detected by the encoder for motor and is inputted to the drive control section through the motor drive cable 134 and the third contact portion 119.

A relay gear 144 is attached to the motor shaft 141a. A drive gear 145 which is meshed with the relay gear 144 is provided at the drive shaft 143. The relay gear 144 and the drive gear 145 configure a reduction gear mechanism.

A shaft (not shown) of the drive shaft 143 is inserted through the universal cord 103 in a manner extending along a longitudinal axis (not shown) of the universal cord 103. More specifically, the drive shaft 143 is inserted through a guide tube 146 extendedly installed inside the universal cord 103 along the longitudinal axis and having a through hole as a guide channel. A distal end of the guide tube 146 is fixed to a tube fixing member 147 provided inside the operation section 102, and a proximal end is fixed to a tube fixing portion 173 provided at the connector framework part 170 as shown in FIG. 8.

The drive shaft 143 is a flexible shaft, a torque coil, which is a multi-threaded, multi-layered coil, or a torque wire, for example. In the present embodiment, the drive shaft 143 is a multi-threaded, multi-layered coil having two coil layers, for example, and is formed by spirally winding special hard steel wires or stainless steel wires for spring clockwise and counterclockwise alternately around the shaft axis to form several layers.

Moreover, the drive shaft 143 is formed of a wire rod of a wire diameter selected in advance, and torsional rigidity is set so as to achieve predetermined torsional characteristics at the time of rotation in a winding direction. More specifically, the torsional rigidity of the drive shaft 143 is set lower than torsional rigidity of the universal cord 103. In other words, the torsional rigidity of the universal cord 103 is higher than the torsional rigidity of the drive shaft 143.

The drive shaft 143 transmits a driving force of the motor 141 to the pulley 142. A bevel gear 151 for pulley is fixedly installed for the purpose at a shaft distal end portion, of the drive shaft 143, positioned on the pulley 142 side.

That is, end portions of the drive shaft 143 protrude from a distal end surface and a proximal end surface of the guide tube 146.

Inside the operation section 102, the rotatable pulley 142, a potentiometer 136 for pulley for detecting an amount of rotation of the pulley 142, and a potentiometer 135 for knob shaft are provided.

The potentiometer 135 for knob shaft detects an amount of rotation of a knob shaft 108*a* of the up-down bending operation instruction knob 108. A distal end of the first signal cable 132 is connected to the potentiometer 135 for knob shaft. A detection signal of the potentiometer 135 for knob shaft is outputted to the drive operation input section through the first signal cable 132 and the first contact portion 118. Then, the drive control section outputs, to the motor 141, a drive signal corresponding to the detection signal of the potentiometer 135 for knob shaft so as to cause the bending section 122 to perform a bending movement.

A distal end of the second signal cable 133 is connected to the potentiometer 136 for pulley. A detection signal of the potentiometer 136 for pulley is outputted to the drive operation input section through the second signal cable 133 and the second contact portion 119.

The pulley 142 bends the bending section 122 in an upward direction or a downward direction by being rotated and pulling or loosening bending wires 148, 149. Accordingly, a proximal end of the upward bending wire 148, a distal end of which is fixedly installed at a predetermined up direction position of the bending section 122, and a proximal end of the downward bending wire 149, a distal end of which is fixedly installed at a predetermined down direction position of the bending section 122, are provided at the pulley 142.

The pulley 142 is provided with a driving force receiving section. The driving force receiving section is configured of a driving force receiving bevel gear 152 as an input section which is provided inside the operation section 102 and which is meshed with the bevel gear 151 for pulley, a first spur gear 153, and a second spur gear 154.

The second spur gear 154 is integrated with the pulley 142. The pulley 142 is capable of rotating together with the second spur gear 154. The first spur gear 153 is integrated with the driving force receiving bevel gear 152. The driving force receiving bevel gear 152 is capable of rotating together with the first spur gear 153. Moreover, the first spur gear 153 and the second spur gear 154 are in a meshed state.

In the present embodiment, the driving force receiving section and the pulley 142 are driven members, and when the motor shaft 141*a* of the motor 141 is rotated clockwise when seen from a direction of an arrow Y8, for example, the relay gear 144 as an output section is rotated and the drive gear 145 is rotated. When the drive gear 145 is rotated, the drive shaft 143 rotates in a direction of an arrow Yr in the drawing. A rotational driving force of the drive shaft 143 is transmitted to the pulley 142 through the driving force receiving section described above.

As a result, the pulley 142 is rotated in a direction of an arrow Yp in the drawing. Then, the upward bending wire 148 is pulled in a direction of an arrow Yu in the drawing, and the bending section 122 is bent in the upward direction. Furthermore, when the pulley 142 is rotated in an opposite direction from the direction of the arrow Yp in the drawing, the downward bending wire 149 is pulled in a direction of an arrow Yd in the drawing, and the bending section 122 is bent in the downward direction.

Figure 9:
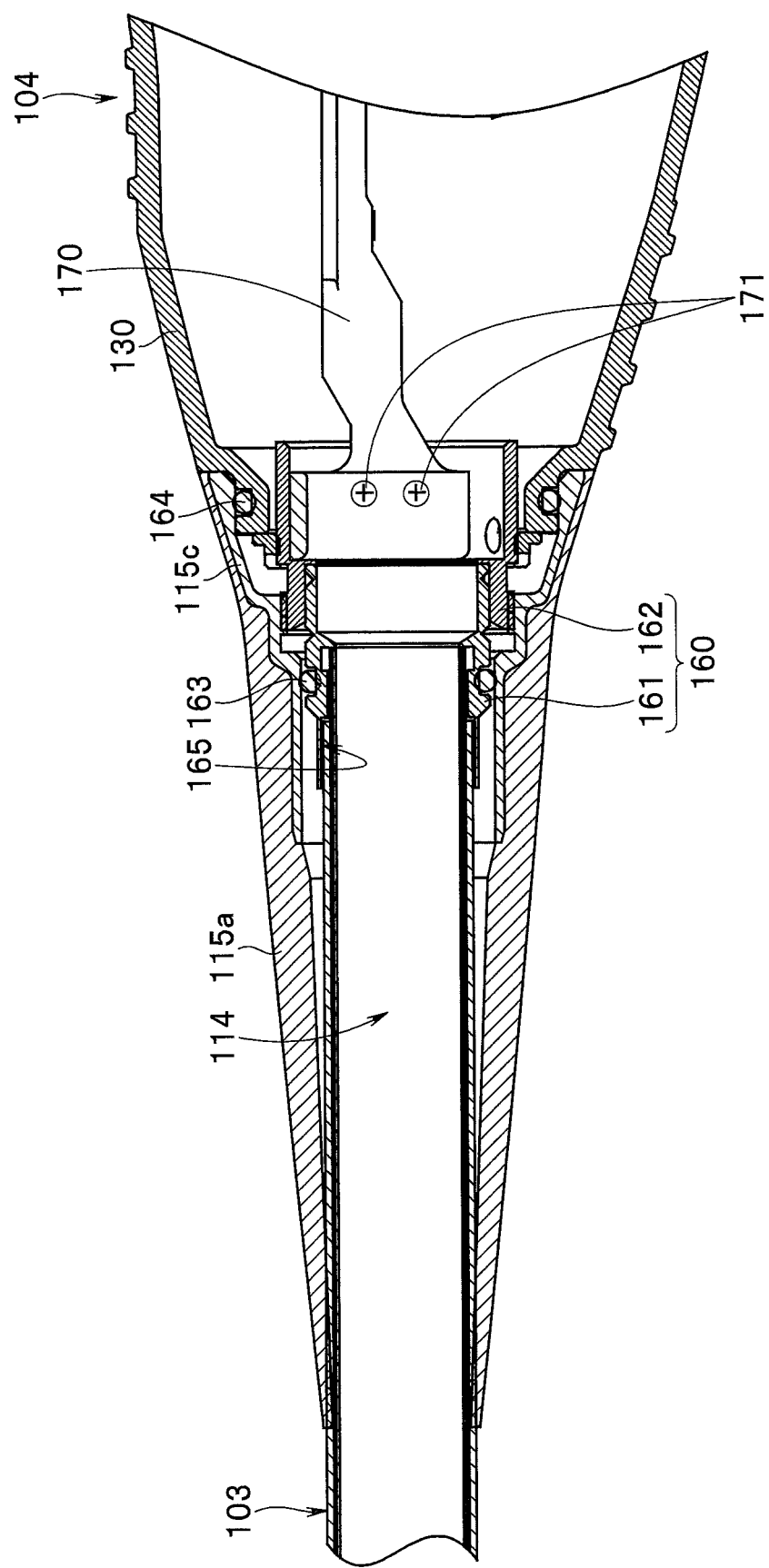
FIG. 9 is a diagram describing an example of a configuration of a universal cord according to the second embodiment.
Figure 10:
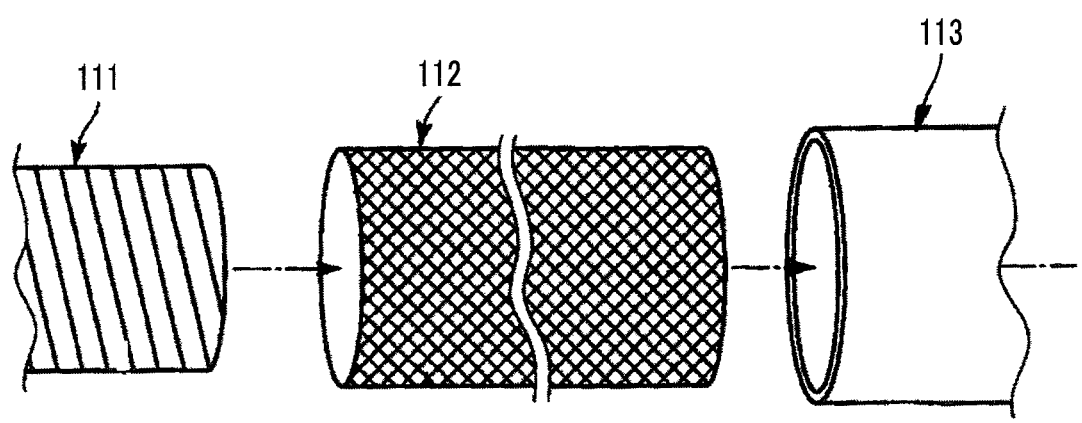
FIG. 10 is a diagram describing a fixing structure of the universal cord and a connector main body according to the second embodiment.

The universal cord 103 described above is formed as a layered tube member stacking the helical tube 111, the flexible reticular tube 112, and the flexible envelope 113 shown in FIG. 10. The end portions of the universal cord 103 shown in FIG. 9 have a same configuration, and one end portion is fixedly installed at the connector main body 130 and the other end portion is fixedly installed at the operation section main body 150.

A description will now be given of a configuration of an end portion on one side which is fixedly installed at the connector main body 130. Note that a configuration of the other end portion is the same as the configuration of the end portion on one side, and a description of the configuration of the other end portion will be omitted.

As shown in FIG. 9, the end portion of the universal cord 103 is fixed to the connector main body 130 through a cable pipe sleeve 160. A reference sign 115*c* is a bend preventing insertion member which is of metal and which is formed into a predetermined shape.

The cable pipe sleeve 160 is provided at the end portion of the universal cord 103. For example, the cable pipe sleeve 160 is configured by including a first pipe sleeve 161, and a second pipe sleeve 162.

More specifically, a distal side portion of the first pipe sleeve 161 is a universal cord fixing portion 165, and an outer peripheral surface of the flexible reticular tube 112 exposed at the end portion of the universal cord 103 is disposed on an inner surface of the universal cord fixing portion 165, and the universal cord fixing portion 165 and the flexible reticular tube 112 are integrally bonded and fixed by an adhesive or the like while maintaining liquid-tightness.

The second pipe sleeve 162 is bonded and fixed to an end portion of the first pipe sleeve 161 by an adhesive not shown. Two screw holes (not shown) are provided at predetermined positions of the second pipe sleeve 162. Screws 171 for integrally fixing the connector framework part 170 disposed on an inner peripheral surface of the second pipe sleeve 162 are placed in the screw holes.

Accordingly, the connector framework part 170 and the universal cord 103 are integrated by the cable pipe sleeve 160.

Effects of the endoscope 2A configured in the above manner will now be described.

For example, at the time of inserting the insertion section 101 into an intestinal tract, a surgeon holds the flexible tube section 123 of the insertion section 101 with the right hand, and inserts the insertion section 101 towards a deep region while causing the bending section 122 to perform a bending movement in the up-down/left-right directions by operating the bending operation instruction knobs 108, 109 with the left hand as necessary.

As described above, when the bending operation knob 108 or 109 is operated, the motor 141 is driven, and rotation of the motor shaft 141a is transmitted to the drive gear 145 through the relay gear 144 to rotate the drive shaft 143. Then, a rotational driving force of the drive shaft 143 is transmitted to the pulley 142, and the bending wires 148, 149 are pulled/loosened according to rotation of the pulley 142, and the bending section 122 is bent.

When the insertion section 3 is being moved in the intestinal tract towards a deep region, the flexible tube section 123 possibly passes through a bent portion of the intestinal tract. Here, due to the flexible tube section 123 being bent with a small bending radius, disposed positions of endoscope internal components inserted through and disposed in the flexible tube section 123 may be changed and movement of the bending wires 148, 149 may be prevented. Moreover, when movement of the bending wires 148, 149 is prevented, rotation of the pulley 142 is stopped.

However, the motor shaft 141a keeps rotating even when rotation of the pulley 142 is stopped. However, because rotation of the pulley 142 is stopped, rotation of the motor shaft 141a is not transmitted to the drive shaft 143 through the relay gear 144 and the drive gear 145 to rotate the drive shaft 143.

Accordingly, during rotation of the relay gear 144 according to rotation of the motor shaft 141a, a torsional force is applied to the drive shaft 143. On the other hand, when rotation of the drive shaft 143 is disabled, an external force acts to cause the relay gear 144 to revolve around the drive gear 145. In the present case, because the motor 141 is integrally fixed to the motor fixing portion 172 of the connector framework part 1170, the relay gear 144 does not revolve, and the external force is transmitted to the motor 141 through the motor shaft 141a to which the relay gear 144 is attached.

Then, the external force transmitted to the motor 141 acts as a torsional force on the connector framework part 1170. The connector framework part 1170 is integrated with the universal cord 103 through the cable pipe sleeve 160, and thus, the torsional force acts as a torsional force on the universal cord 103. As a result, a torsional force acts on the universal cord 103.

In the present embodiment, torsional rigidity of the universal cord 103 is set higher than torsional rigidity of the drive shaft 143. As a result, twisting of the connector framework part 170 inside the connector main body 130 and damaging of the universal cord 103 before the drive shaft 143 may be reliably prevented, in a state where rotation of the pulley 142 is stopped and a torsional force is applied to the universal cord 103.

Accordingly, a situation where the endoscope 2A provided with the electric bending mechanism as the insertion assisting mechanism has to be repaired due to the universal cord 103 being damaged before the drive shaft 143 is prevented.

Note that the cable pipe sleeve 160 is described above as including the first pipe sleeve 161 and the second pipe sleeve 162. However, the cable pipe sleeve may alternatively be configured by integrating the first pipe sleeve 161 and the second pipe sleeve 162.

A reference sign 163 is a first O-shaped ring. The first O-shaped ring 163 is provided on an outer peripheral surface of the first pipe sleeve 161 and is in close contact with an inner surface of the bend preventing insertion member 115c.

A reference sign 164 is a second O-shaped ring. The second O-shaped ring 164 is provided on a distal side outer peripheral surface of the connector main body 130 disposed on a proximal side outer peripheral surface of the second pipe sleeve 162 and is in close contact with the inner surface of the bend preventing insertion member 115c.

In the present embodiment, the universal cord 103 may be reliably prevented from being damaged by a torsional force before the drive shaft 143, in a state where a rotational driving force of the motor 141 is transmitted to the pulley 142 through the drive shaft 143 and the bending section 122 is performing a bending movement.

Accordingly, a situation where the endoscope provided with the electric bending mechanism has to be repaired due to the universal cord 103 being damaged before the drive shaft 143 is prevented.

In the present embodiment, the bending operation knobs 108, 109 are cited as the operation instruction members to be operated to bend the bending section 122. However, the operation instruction members are not limited to the knobs 108, 109, and may be a joystick or a trackball, for example.

Note that the present invention is not limited to the embodiments described above, and various modifications may be made within the scope of the invention. The insertion appliance is not limited to an endoscope, and may alternatively be a treatment instrument for endoscope which is inserted through a treatment instrument channel of an endoscope, a guide tube for guiding an endoscope into a body, or the like. In such a case, the insertion device is mounted on an insertion section of the treatment instrument for endoscope, or on an insertion section of the guide tube.

According to the present invention, an insertion device can be realized, which is configured to prevent, without impairing a function of an electric mechanism section, a tube body, including a coiled tube and where a rotational drive source or a driven member is disposed, from being damaged due to a torsional force from the rotational drive source or a torsional force from the driven member, before a transmission member which is configured to transmit, to the driven member, a rotational force of the rotational drive source provided at the electric mechanism section.

The present invention is not limited to the embodiments described above, and various changes and modifications may be made within the scope of the present invention.

What is claimed is:
1. An insertion device comprising:
an insertion section configured for insertion into a body cavity;
an operation section arranged on a proximal side of the insertion section;
a universal cord extending in a long axis direction, the universal cord having a distal side connected to the operation section, the universal cord including a helical tube, a mesh tube, and an envelope arranged in order radially outward from a central axis;
a drive source disposed on a proximal side of the universal cord;
a driven member disposed on the distal side of the universal cord; and
a transmission member provided inside the helical tube of the universal cord in a manner extending along the long axis direction of the universal cord, the transmission member being driven to perform rotation around an extension axis by a driving force of the drive source to transmit the rotation to the driven member, wherein
a thickness of the helical tube, a diameter of a wire of the mesh tube, a thickness of the envelope, and a hardness of a resin of the envelope are set such that a first torsional resistance of the universal cord around the central axis is higher than a second torsional resistance, around the extension axis, of the transmission member extending from an output portion of the drive source to an input portion of the driven member.

2. The insertion device according to claim 1, wherein the driven member is configured to cause an external device rotatably attached to the insertion section to rotate.

3. The insertion device according to claim 1, wherein the driven member is configured to cause a bending section provided on a distal side of the insertion section to perform a bending movement.

4. The insertion device according to claim 1, wherein the drive source is disposed inside a housing provided on a proximal side of the universal cord.

5. The insertion device according to claim 1, wherein the transmission member is a coil formed of a wire rod of a predetermined wire diameter helically wound around the long axis, the transmission member being set to have the second torsional resistance to be lower than the first torsional resistance of the universal cord when the transmission member is rotated in a winding direction of the wire rod.

6. The insertion device according to claim 5, wherein the coil is formed as a multi-layered coil comprising two wire rods of a predetermined wire diameter helically wound in a layered form, the coil being set to have the second torsional resistance lower than the first torsional resistance of the universal cord.

7. The insertion device according to claim 6, wherein the multi-layered coil includes at least two coil layers with different winding directions.

8. The insertion device according to claim 1, further comprising a reduction gear mechanism coupling the drive source and the transmission member to each other.

\* \* \* \* \*